United States Patent
Zupancic (12)

(10) Patent No.: US 7,745,664 B2
(45) Date of Patent: Jun. 29, 2010

(54) PROCESSES FOR PREPARING VENLAFAXINE AND VENLAFAXINE HYDROCHLORIDE OF FORM I

(75) Inventor: Silvo Zupancic, Novo mesto (SI)

(73) Assignee: KRKA Tovarno Zdravil, d.d. Novo Mesto, Novo mesto (SI)

( * ) Notice: Subject to any disclaimer, the term of this patent is extended or adjusted under 35 U.S.C. 154(b) by 0 days.

(21) Appl. No.: 10/583,439

(22) PCT Filed: Dec. 10, 2004

(86) PCT No.: PCT/EP2004/014102

§ 371 (c)(1), (2), (4) Date: Jun. 16, 2006

(87) PCT Pub. No.: WO2005/058796

PCT Pub. Date: Jun. 30, 2005

(65) Prior Publication Data

US 2007/0185354 A1    Aug. 9, 2007

(30) Foreign Application Priority Data

Dec. 16, 2003  (DE)  ................. 103 59 154

(51) Int. Cl.
  *C07C 211/00*  (2006.01)
  *C07C 205/00*  (2006.01)

(52) U.S. Cl. .............. 564/336; 568/705; 568/708
(58) Field of Classification Search ............. 564/336; 568/705, 708
See application file for complete search history.

(56) References Cited

U.S. PATENT DOCUMENTS 6,924,393 B2 * 8/2005 Dolitzky et al. ............. 564/336

FOREIGN PATENT DOCUMENTS

| EP | 0112669 | 7/1984 |
| EP | 0797991 | 10/1997 |
| WO | WO 02/45658 | 6/2002 |
| WO | WO 02/50017 | 6/2002 |
| WO | WO 03/050074 | 6/2003 |

OTHER PUBLICATIONS

John P. Yardley, et al., 2-Phenyl-2-(1-hydroxycycloalkyl)ethylamine Derivatives: Synthesis and Antidepressant Activity, J. Med. Chem., vol. 33, p. 2899-2905 (1990).

* cited by examiner

*Primary Examiner*—Sikarl A Witherspoon
(74) *Attorney, Agent, or Firm*—Cohrn Pontani Lieberman & Pavane LLP

(57) ABSTRACT

A process for preparing venlafaxine in a high yield as well as processes for producing venlafaxine hydrochloride of form I having a very high polymorphic purity are described.

8 Claims, No Drawings

PROCESSES FOR PREPARING VENLAFAXINE AND VENLAFAXINE HYDROCHLORIDE OF FORM I

PRIORITY CLAIM

This is a U.S. national stage of application No. PCT/EP2004/014102, filed on Dec. 10, 2004. Priority is claimed on the following application(s): Country: Germany, Application No.: 103 59 154.0, Filed: Dec. 16, 2003; the content of which is incorporated here by reference.

TECHNICAL FIELD

The present invention belongs to the field of organic chemistry and relates to processes for the preparation of venlafaxine and venlafaxine hydrochloride of polymorphic form I. The invention also relates to venlafaxine hydrochloride of form I which is obtainable by these processes.

TECHNICAL PROBLEM

It is known in the pharmaceutical field that important properties of polymorphs of a drug, e.g. dissolution rate, bioavailability, and chemical stability, can differ substantially. Technological considerations also require morphologically uniform product which can be prepared in a reproducible manner. Additionally, the preparation of a drug needs to be as efficient as possible so that there is always the desire to improve the yields of corresponding processes.

Prior art processes for preparing venlafaxine do not provide the desired yields. Moreover, the product is often contaminated with substantial amounts of by-product and a long time is required to complete the reaction.

Prior art processes for preparing venlafaxine hydrochloride of form I suffer in particular from the drawbacks that they do not lead to satisfactory purity and yield of the product. Additionally, these processes often involve also the use of solvents which are not acceptable form an ecological standpoint and they cannot be carried out satisfactorily on an industrial scale. Finally, the reaction conditions of these processes are often difficult to control such that only the desired polymorph I having a high purity is produced.

Consequently, it is an object of the present invention to provide improved processes for preparing venlafaxine and for preparing venlafaxine hydrochloride of form I which do not suffer from the above mentioned disadvantages.

These object is achieved by the process for preparing venlafaxine and the process for preparing venlafaxine hydrochloride of form I described below.

The invention is also directed to the venlafaxine hydrochloride of form I.

BACKGROUND OF THE INVENTION

Venlafaxine is the INN for 1-(2-dimethylamino-1-(4-methoxyphenyl)-ethyl)-cyclohexanol. Its racemic hydrochloride salt is included in a formulation which is commercially available under the trade name Effexor. Venlafaxine is used in form of its salt as this allows an easy preparation of various types of formulations, such as tablets, capsules, lozenges, powders, and the like for oral administration.

Venlafaxine was first described in EP-A-112 669. According to this document venlafaxine is prepared by N-methylation of the precursor N,N-didesmethyl venlafaxine using formaldehyde and formic acid. The venlafaxine is then recovered by chromatography to remove the by-product spiro venlafaxine and it is subsequently converted into venlafaxine hydrochloride using 4N isopropanolic HCl. The yield of the product, however, was very low.

In Journal of Medicinal Chemistry, 1990, Vol. 33, No. 10 (2899-2905) the synthesis of venlafaxine from p-methoxybenzylcyanide is disclosed and it involves N-methylation by a modified Eschweiler-Clark procedure using formaldehyde and formic acid. A solution of venlafaxine in ethyl acetate is treated with 2-propanolic HCl and the obtained venlafaxine hydrochloride is then recrystallized from methanol/ethyl acetate under unspecified conditions. The calculated yield for the crude product is 80%, based on N,N-didesmethyl venlafaxine.

The existence of certain polymorphs of venlafaxine hydrochloride is mentioned in EP-A-797 991. In this document, two polymorphs are described one of them being regarded as a kinetical product of the crystallization process. It is also disclosed that on heating in the crystallization solvent one of the polymorph is transformed into the other polymorph. It is, however, not disclosed which solvent is used for recrystallization.

Later on, various patent applications were published disclosing different polymorphic forms of racemic venlafaxine hydrochloride, e.g. designated as Form I, II, III and IV and A, B, C and D, and processes for their preparation.

WO 02/45658 describes the preparation of crystalline venlafaxine from N,N-didesmethyl venlafaxine hydrochloride and processes for producing crystalline venlafaxine hydrochloride forms I, II, III and IV. The products obtained were often mixtures of polymorphs which underlines the criticality of the conditions used. Venlafaxine hydrochloride form I is said to be obtainable by reacting a solution of venlafaxine in isopropanol and exposing the solution to gaseous HCl. The reaction mixture is cooled, filtered and dried. The yield of the product is, however, not given. An alternative method for preparing venlafaxine hydrochloride form I comprises dissolving venlafaxine hydrochloride in methanol under reflux and adding an anti-solvent selected from ethylacetate, isopropyl ether or methyl t-butyl ether and converting the obtained form III to form I by drying at about 60° C.

WO 02/36542 discloses also polymorphic forms of venlafaxine hydrochloride which are designated as forms A, B, C and D and processes for their preparation.

WO 02/50017 describes the N-methylation of N,N-didesmethyl venlafaxine which can also be used in form of its formic acid salt.

WO 03/050074 describes a process for preparing venlafaxine hydrochloride form I by reacting venlafaxine with gaseous HCl in various solvents, namely ethyl acetate, acetonitrile, acetone and methylisobutyl ketone. The calculated yield of the product obtained is only 50%, based on the starting material N,N-didesmethyl venlafaxine. It is further disclosed that numerous factors are influencing the type of polymorph which is produced and its purity.

It is apparent from the above documents that most known venlafaxine hydrochloride polymorphs are prepared by using venlafaxine hydrochloride in different solvents and under different reaction conditions. Such parameters appear to play a major role in the formation of different polymorphs having different crystalline structures. These parameters may include presence of co-solvents, the temperature at which hydrochloride formation occurs, whether or not refluxing of the reaction mixture after hydrochloride formation is effected and the temperature at which the filtration of hydrochloride salt is performed.

Since venlafaxine hydrochloride is marketed as a racemate, polymorphism is to be dealt with great care, especially since the form which is more thermodynamically stable and shows desired bioavailability would be preferred over other forms considering storage conditions and shelf life. The less thermodynamically stable form is prone to convert into a more stable form and such forms are not good candidates for pharmaceutical applications, since this conversion will be noticed during the storage of the material.

It has now been surprisingly found that the process according to the invention for preparing venlafaxine hydrochloride form I allows an easy and reproducible way to obtain this product in high yields and especially important with a very high polymorphic purity.

It has further been found out that the process according to the invention for preparing venlafaxine avoids the formation of substantial amounts of by-products and proceeds quickly to completion and hence results in high yields of venlafaxine in an economical manner.

DETAILED DESCRIPTION OF THE INVENTION

In a first aspect, the invention relates to a process for preparing venlafaxine which comprises
(a) converting a venlafaxine precursor selected from the group of N,N-didesmethyl venlafaxine of formula (I), a salt thereof, spiro venlafaxine of formula (II) and a salt thereof

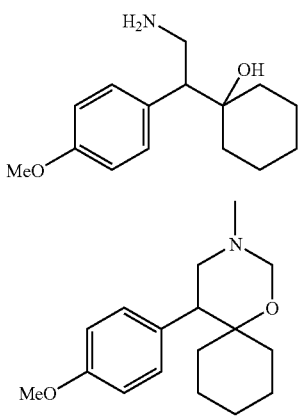

to venlafaxine, wherein the conversion is carried out in the presence of a salt of formic acid which is selected from the group of a metal salt or an ammonium salt of formic acid, and
(b) optionally reacting the venlafaxine with an acid to prepare an acid addition salt of venlafaxine.

It has surprisingly been found out that the presence of the specific salt of formic acid allows the N-methylation of the precursors not only to proceed very quickly, but also with a high yield avoiding the formation of undesirable by-products. It is assumed that this is caused by an accelerating action the formic acid salt has on the conversion of spiro venlafaxine, which is likely an intermediary product in the N-methylation of N,N-didesmethyl venlafaxine and only slowly reacts to venlafaxine. This is illustrated by the following reaction scheme showing a preferred embodiment of the process.

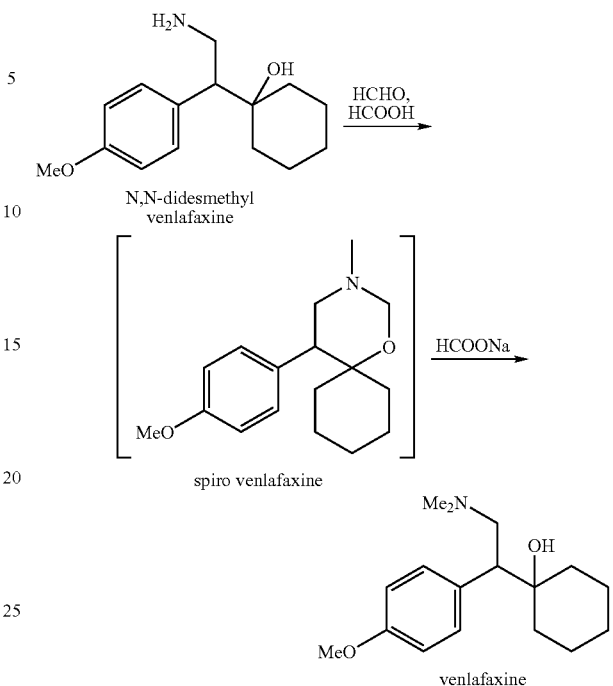

It is preferred that the salt of formic acid is used in such an amount that the molar ratio of the salt of formic acid to the venlafaxine precursor is 0.3-10 to 1, in particular 0.5-3 to 1. This leads to a particularly smooth and complete reaction.

Further, it is preferred that the metal salt of formic acid is an alkali or earth alkaline metal salt of formic acid. Examples of especially preferred salts are the Na, K or Li salt. The $NH_4$ salt is also operable.

The salt of formic acid can be present by adding it to the reaction mixture. It is, however, also possible to generate the formic acid salt in-situ in the reaction mixture.

For carrying out step (a) the selected venlafaxine precursor is normally dissolved in a suitable solvent, such as water or other polar solvents like DMF or DMSO. The concentration of the venlafaxine precursor in the solution is preferably 0.2 to 3 mol/l, in particular 0.5 to 1.5 mol/l.

The conversion in step (a) to venlafaxine is preferably carried out by using N,N-didesmethyl venlafaxine or a salt thereof, such as the HCl addition salt. It is, moreover, preferably carried out in the presence of formaldehyde and formic acid. This conversion can also be designated as a N-methylation. The amount of formic acid is usually 2 to 20 equivalents, relative to the venlafaxine precursor. The amount of formaldehyde is usually 2 to 15 equivalents, relative to venlafaxine precursor.

A very convenient way to carry out this conversion is by effecting the conversion in the presence of also an alkali metal or earth alkaline metal hydroxide or $NH_4OH$ in such an amount that it forms in-situ the salt of formic acid. Thus, these metal hydroxides or $NH_4OH$ react with the also present formic acid under in-situ production of the corresponding formic acid salt. In case of use of an acid addition salt of N,N-didesmethyl venlafaxaine, like the HCl salt, it needs to be taken into consideration that these hydroxides also react with the acid of the addition salt. Thus, their amount needs to be such that still the desired amount of formic acid salt is produced.

Preferably, the alkali metal hydroxide is NaOH which forms in-situ Na formiate.

It is further preferred that the mixture of venlafaxine precursor, formaldehyde and formic acid in a selected solvent is heated under reflux for 2 h to 24 h, preferably for 3 h to 7 h.

After completion of the reaction, the mixture is usually adjusted to a pH value of about 12 by using e.g. NaOH.

In a preferred alternative embodiment, the mixture could also be first adjusted to a pH value of about 1 by using HCl, extracted with an organic solvent and then adjusted to a pH value of about 12 by using e.g. NaOH. This procedure allows the removal of a pink impurity often observed.

The venlafaxine can then be extracted with an organic solvent. Preferred are those organic solvents which could be used for an azeotropic distillation of water and are not miscible with water, e.g. isopropyl acetate, propyl acetate, butyl acetate, isobutyl acetate, t-butyl acetate and cyclohexane.

After possible further workup venlafaxine is obtained having a high purity of preferably more than 98 area %, determined by HPLC.

This venlafaxine can optionally in step (b) be reacted with an acid to prepare an acid addition salt of venlafaxine.

In a second aspect, the invention relates to a process for preparing venlafaxine hydrochloride of form I, wherein venlafaxine hydrochloride of form I is crystallized from a solution of venlafaxine hydrochloride in an organic solvent which solvent contains isopropyl acetate and/or cyclohexane.

It has surprisingly been found out that the use of a solvent which contains isopropyl acetate and/or cyclohexane allows the easy and reproducible production of venlafaxine hydrochloride of very high polymorphic purity. Cyclohexane offers the additional benefit of having a high hydrolytical stability.

It is preferred that the solvent consists of isopropyl acetate and/or cyclohexane.

In a first preferred embodiment of this second aspect of the invention, venlafaxine hydrochloride is prepared by reacting venlafaxine with aequous HCl. The amount of the aequous HCl is usually 0.85 to 1.5 equivalents and preferably 0.9 to 1.2 equivalents.

It is further preferred in this embodiment that subsequent to this reaction, the water content of the solution of venlafaxine hydrochloride is less than 3% by weight and preferably less than 1.5% by weight, as determined by the Karl-Fischer method. This is preferably achieved by subjecting the solution to an azeotropic distillation.

Further, it was shown that particularly good results were achieved in this embodiment when the crystallization is effected at a temperature of the solution which is equal or greater than 30° C. below the boiling temperature of the solution, preferably the crystallization is effected at about the boiling temperature of the solution.

It is further preferred in this embodiment to stir the obtained suspension at reflux temperature, preferably for up to 3 h.

The obtained product is venlafaxine hydrochloride form I having a very high purity (HPLC Area %: over 99.5%). This product is identical with the crystalline form for which an x-ray structure determination was disclosed in Acta Crystallographica (2000) C56, 1009-1010.

In a second preferred embodiment of this second aspect of the invention, the solution of venlafaxine hydrochloride is prepared by reacting venlafaxine with a solution of HCl in an alcohol. The alcohol is preferably methanol, ethanol and/or isopropanol. After addition of the solution of HCl the mixture is preferably stirred for up to 4 h.

It is further preferred in this embodiment that venlafaxine hydrochloride of form I is added to the venlafaxine, in particular in an amount of up to 10% by weight, preferably up to 5% by weight, based on venlafaxine. This addition is preferably effected before carrying out the reaction of venlafaxine with the solution of HCl in an alcohol.

Moreover, in this embodiment the crystallization is preferably effected at a temperature of the solution of venlafaxine hydrochloride which is about 20° C.

Also this embodiment of the process allows the production of venlafaxine hydrochloride form I having a very high purity (HPLC Area %: over 99.5%).

In a third aspect, the invention relates to a process for preparing venlafaxine hydrochloride of form I, wherein
(a) a solution of venlafaxine in an organic solvent is reacted with aequous HCl, and
(b) the water content of the resulting solution of venlafaxine hydrochloride is adjusted to less than 3% by weight and preferably less than 1.5% by weight, and
(c) the venlafaxine hydrochloride of form I is crystallized.

The adjustment of the water content in step (b) is preferably effected by subjecting the solution to an azeotropic distillation.

Thus, this process does not necessarily require use of the specific solvent isopropyl acetate and/or cyclohexane as according to the second aspect of the invention. The organic solvent in step (a) is preferably isopropyl acetate and/or cyclohexane, but can also be e.g. propyl acetate, butyl acetate, isobutyl acetate, t-butyl acetate.

The crystallization in step (c) is preferably carried out in accordance with the procedures given above for the first embodiment of the second aspect of the invention.

The processes according to the second and third aspect of the invention are preferably carried out in such a manner that venlafaxine is used which has been prepared according to the process which forms the first aspect of the invention. This results in highly satisfactory yields of more than 85% venlafaxine hydrochloride of form I, based on the amount of venlafaxine precursor used. Prior art processes just deliver yields in the region of 50% for this reaction sequence.

The processes according to the second and third aspect of the invention show the additional advantage that they are able to produce venlafaxine hydrochloride of form I having an average particle size of less than 50 µm, preferably a particle size in the range of 10 to 40 µm. This average particle size is determined by laser diffraction, e.g. using a Mastersizer S Malvern apparatus. Such a particle size is very advantageous as it facilitates the inclusion of the venlafaxine hydrochloride form I in a variety of different pharmaceutical formulations.

In a fourth aspect, the invention also relates to venlafaxine hydrochloride of form I which is obtainable by the above processes. Preferably, the venlafaxine hydrochloride of form I has a purity of more than 99.5 area %, as determined by HPLC. The HPLC method used for determining this purity value was a gradient method with the following equipment/conditions:

Column: Prontosil 300-5-C18-ace-EPS, 5 µm, 250×4.6 mm
Temperature of the column: 20° C.
Detection: UV detector at 227 nm
Flow: 1.2 ml/min
Mobile phase: Solvent A: 0.05 M $NaH_2PO_4$ solution, pH of 6.5
Solvent B: acetonitrile The invention is in the following further illustrated by means of examples.

EXAMPLES

Example 1

Preparation of venlafaxine from N,N-didesmethyl venlafaxine hydrochloride

A 50% aqueous NaOH solution (4 ml, 74 mmol) was added to a stirred solution of N,N-didesmethyl venlafaxine hydrochloride (5.72 g, 20 mmol) in water (16 ml) at room temperature. Formic acid (98%, 11.5 ml, 305 mmol) and 37% aqueous solution of formaldehyde (8.4 ml, 113 mmol) were added to this mixture. The mixture was stirred under reflux temperature and the conversion was completed in 5 h (HPLC: 98.67 area %). Then the solution was cooled to room temperature and adjusted with 50% aequous NaOH to pH 12. The mixture was extracted twice with 66 ml of isopropyl acetate. The collected organic phases were washed three times with water (66 ml). The isolated solution of venlafaxine base was very pure (HPLC: 98.9 area %).

Example 2

Preparation of Venlafaxine Hydrochloride Form I from the Solution of Venlafaxine Base in Isopropyl Acetate To the solution of venlafaxine base in isopropyl acetate from example 1 (66 ml, 10 mmol) 5 ml of 2 M aqueous HCl were added. The mixture was heated and water was removed by azeotropic distillation using a Dean-Starck trap. When all water was removed from the mixture, the product began slowly to crystallize. The obtained suspension was heated under reflux temperature for 1.5 h, then cooled and filtered. 2.75 g (88% from N,N-didesmethyl venlafaxine hydrochloride) of pure venlafaxine hydrochloride form I (HPLC: 99.65 area %) were obtained.

Example 3

Preparation of Venlafaxine Hydrochloride Form I from the Solution of Venlafaxine Base in Isopropyl Acetate The solution of venlafaxine in isopropyl acetate from example 1 (66 ml, 10 mmol) was concentrated to ½ of the volume. Then 10 to 50 mg of venlafaxine hydrochloride form I was added to the solution. Subsequently, a 2.5 M solution of HCl in ethanol (4.0 ml) was slowly added within 30 min. After the whole amount of acid was added, the obtained suspension was stirred for another 2 h. Then the mixture was filtered and the product was washed with isopropyl acetate and dried. We obtained 2.69 g (86% from N,N-didesmethyl venlafaxine hydrochloride) of pure venlafaxine hydrochloride form I (HPLC: 99.65 area %).

What is claimed is:

1. Process for preparing an acid addition salt of venlafaxine which comprises:
   (a) converting a venlafaxine precursor selected from the group consisting of N,N-didesmethyl venlafaxine of formula (I), a salt thereof, spiro venlafaxine of formula (II), and a salt thereof

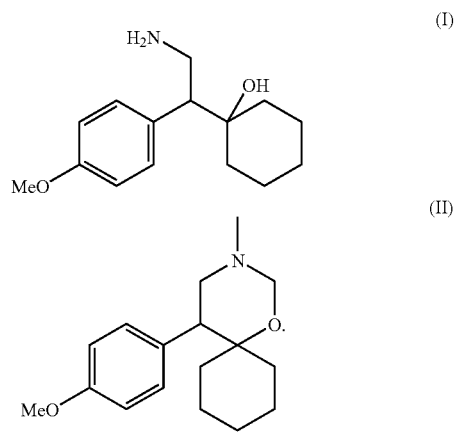

to venlafaxine in an aqueous solution, wherein the conversion is carried out in the presence of a salt of formic acid which is selected from the group consisting of a metal salt and an ammonium salt of formic acid, and wherein the molar ratio of the salt of formic acid to the venlafaxine precursor is 0.3-10 to 1,
   (b) extracting venlafaxine from the aqueous solution with a water-immiscible organic solvent to obtain an organic venlafaxine solution; and
   (c) reacting the organic venlafaxine solution with an acid to prepare the acid addition salt of venlafaxine.

2. Process according to claim 1, wherein the molar ratio is 0.5-3 to 1.

3. Process according to claim 1, wherein the metal salt of formic acid is an alkali or earth alkaline metal salt of formic acid.

4. Process according to claim 3, wherein the alkali metal salt of formic acid is a Na, K or Li salt.

5. Process according to claim 1, wherein in step (a) N,N-didesmethyl venlafaxine (I) or a salt thereof is converted to venlafaxine in the presence of formaldehyde and formic acid.

6. Process according to claim 5, wherein in step (a) the N,N-didesmethyl venlafaxine (I) is used in form of its HCl addition salt.

7. Process according to claim 5, wherein in step (a) the conversion is effected in the presence of also an alkali metal or earth alkaline metal hydroxide or NH$_4$OH in such an amount that it forms in-situ the salt of formic acid.

8. Process according to claim 7, wherein the alkali metal hydroxide is NaOH which forms in-situ Na formate.

* * * * *